US008623412B2

(12) United States Patent
Farid et al.

(10) Patent No.: US 8,623,412 B2
(45) Date of Patent: Jan. 7, 2014

(54) ABUSE-RESISTANT PHARMACEUTICAL COMPOSITIONS

(75) Inventors: Vaghefi Farid, Burlington, MA (US); Gary G. Liversidge, West Chester, PA (US); Stephen B. Ruddy, Schwenksville, PA (US); Eugene R. Cooper, Berwyn, PA (US)

(73) Assignee: Elan Pharma International Limited, Monksland Athlone County Westmeath (IE)

( * ) Notice: Subject to any disclaimer, the term of this patent is extended or adjusted under 35 U.S.C. 154(b) by 1897 days.

(21) Appl. No.: 10/528,727

(22) PCT Filed: Sep. 23, 2003

(86) PCT No.: PCT/US03/29890
§ 371 (c)(1),
(2), (4) Date: Dec. 5, 2005

(87) PCT Pub. No.: WO2004/026262
PCT Pub. Date: Apr. 1, 2004

(65) Prior Publication Data
US 2006/0104909 A1    May 18, 2006

Related U.S. Application Data

(60) Provisional application No. 60/412,861, filed on Sep. 23, 2002, provisional application No. 60/413,495, filed on Sep. 25, 2002.

(51) Int. Cl.
*A61K 9/14* (2006.01)
*A61K 9/16* (2006.01)
*A61K 9/50* (2006.01)
*A61K 9/44* (2006.01)

(52) U.S. Cl.
USPC ........... 424/484; 424/490; 424/498; 424/502; 424/10.2

(58) Field of Classification Search
None
See application file for complete search history.

(56) References Cited

U.S. PATENT DOCUMENTS

| | | |
|---|---|---|
| 1,174,695 A | 3/1916 | Dawson |
| 1,204,793 A | 11/1916 | Levy |
| 1,204,794 A | 11/1916 | Levy |
| 1,349,326 A | 8/1920 | Davis |
| 1,893,008 A | 1/1933 | Wamescher |
| 2,258,414 A | 10/1941 | Kvalnes |
| 3,260,646 A | 7/1966 | Paulsen |
| 3,402,240 A * | 9/1968 | Cain et al. ............ 424/468 |
| 3,885,027 A | 5/1975 | Shaw et al. |
| 4,070,494 A | 1/1978 | Hoffmeister et al. |
| 4,175,119 A | 11/1979 | Porter |
| 4,493,848 A | 1/1985 | LaHann et al. |
| 4,532,139 A | 7/1985 | Janusz et al. |
| 4,599,342 A | 7/1986 | LaHann |
| 4,812,446 A | 3/1989 | Brand |
| 4,931,277 A | 6/1990 | Fontaine et al. |
| 4,980,169 A | 12/1990 | Oppenheimer et al. |
| 4,997,853 A | 3/1991 | Bernstein |
| 5,008,293 A | 4/1991 | Berger |
| 5,035,882 A | 7/1991 | Hussein et al. |
| 5,209,879 A | 5/1993 | Redding, Jr. |
| 5,296,225 A | 3/1994 | Adekunle et al. |
| 5,716,625 A | 2/1998 | Hahn et al. |
| 5,756,107 A | 5/1998 | Hahn et al. |
| 5,885,597 A | 3/1999 | Botknecht et al. |
| 5,962,532 A | 10/1999 | Campbell et al. |
| 5,985,860 A | 11/1999 | Toppo |
| 6,139,850 A | 10/2000 | Hahn et al. |
| 6,143,353 A | 11/2000 | Oshlack et al. |
| 6,174,891 B1 | 1/2001 | Nagase et al. |
| 6,180,620 B1 | 1/2001 | Salvemini |
| 6,197,823 B1 | 3/2001 | Barr et al. |
| 6,197,830 B1 | 3/2001 | Frome |
| 6,228,863 B1 * | 5/2001 | Palermo et al. ............ 514/282 |
| 6,248,788 B1 | 6/2001 | Robbins et al. |
| 6,277,384 B1 | 8/2001 | Kaiko et al. |
| 6,277,389 B1 | 8/2001 | Pullen |
| 6,277,398 B1 | 8/2001 | Caruso |
| 6,284,797 B1 | 9/2001 | Rhodes |
| 6,375,957 B1 | 4/2002 | Kaiko et al. |
| 6,455,076 B1 | 9/2002 | Hahn et al. |
| 6,696,066 B2 | 2/2004 | Kaiko et al. |
| 6,696,088 B2 | 2/2004 | Oshlack et al. |
| 6,716,449 B2 | 4/2004 | Oshlack et al. |
| 2001/0002406 A1 | 5/2001 | Robbins |
| 2001/0044026 A1 | 11/2001 | Vaghefi et al. |

(Continued)

FOREIGN PATENT DOCUMENTS

| | | |
|---|---|---|
| EP | 0514008 A1 | 11/1992 |
| WO | 95/20947 | 8/1995 |
| WO | 9614058 A | 5/1996 |
| WO | 0108661 A2 | 2/2001 |
| WO | 01/32148 | 5/2001 |
| WO | 0132148 A1 | 5/2001 |
| WO | 01/58447 | 8/2001 |
| WO | 01/58451 | 8/2001 |
| WO | 0158451 A1 | 8/2001 |
| WO | 03039514 A1 | 5/2003 |

*Primary Examiner* — L. R. Draper
(74) *Attorney, Agent, or Firm* — Fox Rothschild LLP

(57) ABSTRACT

An abuse-resistant controlled release pharmaceutical composition comprising a pharmaceutically effective amount of discrete particles of an active capable of abuse, wherein surfaces of said particles are wetted with a water insoluble coating material, and preferably wherein said composition comprises a matrix, in which said particles are distributed, and which renders the abuse-capable compound within the matrix difficult to separate from the matrix; and a method for the preparation of a controlled release pharmaceutical composition having a reduced potential for abuse, comprising applying a pressure force to a mixture comprising a water insoluble material, and particles of a pharmaceutically active compound capable of inducing in a subject a reaction that is physiologically or psychologically detrimental if administered in an immediate release dosage form, thereby resulting in surface coated particles, and incorporating said surface coated particles into a pharmaceutical composition.

7 Claims, No Drawings

(56) References Cited

U.S. PATENT DOCUMENTS

| | | | |
|---|---|---|---|
| 2002/0004509 A1 | 1/2002 | Palermo et al. | |
| 2002/0058048 A1 | 5/2002 | Tamura et al. | |
| 2002/0058050 A1* | 5/2002 | Sackler et al. | 424/401 |
| 2002/0058673 A1 | 5/2002 | Kaiko et al. | |
| 2002/0098210 A1 | 7/2002 | Hahn et al. | |
| 2002/0164373 A1 | 11/2002 | Maloney | |
| 2003/0004177 A1 | 1/2003 | Kao et al. | |
| 2003/0026838 A1 | 2/2003 | Farrell | |
| 2003/0049272 A1 | 3/2003 | Joshi et al. | |
| 2003/0064099 A1 | 4/2003 | Oshlack et al. | |
| 2003/0064122 A1 | 4/2003 | Goldberg et al. | |
| 2003/0065002 A1 | 4/2003 | Caruso et al. | |
| 2003/0068370 A1 | 4/2003 | Sackler | |
| 2003/0068371 A1 | 4/2003 | Oshlack et al. | |
| 2003/0068375 A1 | 4/2003 | Wright et al. | |
| 2003/0068392 A1 | 4/2003 | Sackler | |
| 2003/0091635 A1 | 5/2003 | Baichwal et al. | |
| 2003/0118641 A1 | 6/2003 | Maloney et al. | |
| 2003/0124185 A1 | 7/2003 | Oshlack et al. | |
| 2003/0143269 A1 | 7/2003 | Oshlack et al. | |
| 2003/0157168 A1 | 8/2003 | Breder et al. | |
| 2004/0202717 A1 | 10/2004 | Mehta | |
| 2005/0043327 A1 | 2/2005 | Coe et al. | |
| 2005/0043345 A1 | 2/2005 | Coe et al. | |
| 2005/0112067 A1 | 5/2005 | Kumar et al. | |
| 2005/0163856 A1 | 7/2005 | Maloney et al. | |
| 2005/0192309 A1 | 9/2005 | Palermo et al. | |

* cited by examiner

ABUSE-RESISTANT PHARMACEUTICAL COMPOSITIONS

CROSS-REFERENCE TO RELATED APPLICATIONS

Applicants claim the benefit of PCT Application No. PCT/US03/29890 filed Sep. 23, 2003 which claims the benefit of provisional Application No. 60/412,861, filed Sep. 23, 2002, and 60/413,495, filed Sep. 25, 2002, which are incorporated herein in therein entirety.

FIELD OF THE INVENTION

This invention relates to dosage forms of abusable substances having reduced potential for abuse. In particular, the dosage forms of this invention are intended to administer the abusable substance to the body by oral application.

The potential for abuse by either oral or parenteral routes of narcotic and other psychoactive drugs is well known. For example, the potential for abuse of the synthetic narcotic drug fentanyl is so high that it has become a major cause of death for anesthesiologists and other hospital workers having access to the drug. Another well-known mode of abuse is the crushing of extended release dosage forms to convert the extended release into an immediate release form capable of administration by means including inhalation, injection, and contact with mucous membranes. The extended release opioid drug, Oxycontin, is one example of a formulation capable of abuse. Another popular mode of abuse of oral medications involves the extraction of the opioid from the dosage form, and the subsequent injection of the opioid (using any "suitable" vehicle for injection) in order to achieve a "high."

Many abusable substances are capable of being administered to the body by direct application of the drug to the skin or mucosa, i.e., nasal, vaginal, oral, or rectal mucosa. Typically, a particular dose of an opioid analgesic is more potent when administered parenterally as compared to the same dose administered orally. Compositions suitable for oral administration could be subject to abuse, and it would clearly be desirable to have such compositions or dosage forms available in a condition in which the abuse potential of the composition or dosage form is reduced without diminishing the therapeutic efficacy of the abusable substance to be administered.

It is, accordingly, an object of this invention to provide a composition of matter for oral administration of an abusable substance to a subject, which composition has a low potential for abuse.

REPORTED DEVELOPMENTS

There have previously been attempts in the art to control the abuse potential associated with opioid analgesics. In order to prevent abuse of these substances, dosage forms have been proposed that combine the abusable substance with an amount of an antagonist for the abusable substance sufficient to eliminate the "high" associated with abuse of the substance without eliminating the other therapeutic benefits for which the drugs are intended to be administered. Attempts to curtail abuse have therefore typically centered on the inclusion in the oral dosage form of an opioid antagonist which is not orally active but which will substantially block the analgesic effects of the opioid if one attempts to dissolve the opioid and administer it parenterally.

U.S. Pat. No. 3,773,955 describes orally effective analgesic compositions, which upon parenteral administration do not produce analgesia, euphoria, or physical dependence, and thereby prevent parenteral abuse of the analgesic agents. Such compositions contain naloxone per analgesic oral dose. U.S. Pat. No. 3,493,657 describes compositions comprising naloxone and morphine or oxymorphone, which compositions were said to provide a strong analgesic effect without the occurrence of undesired side effects such as hallucinations. U.S. Pat. No. 4,582,835 describes a method of treating pain by administering a sublingually effective dose of buprenorphine with naloxone. U.S. Pat. No. 4,457,933 describes a method for decreasing both the oral and parenteral abuse potential of strong analgesic agents such as oxycodone, propoxyphene and pentazocine, by combining an analgesic dose of the opioid with naloxone in a specific, relatively narrow range. The dose of naloxone to be combined with the opioid is stated to substantially eliminate the possibility of either oral or parenteral abuse of the opioid without substantially affecting the oral analgesic activity thereof.

U.S. Pat. No. 6,375,957 discloses oral dosage forms comprising a combination of an opioid agonist, acetaminophen and an orally active opioid antagonist, the opioid antagonist being included in a ratio to the opioid agonist to provide a combination product which is analgesically effective when the combination is administered orally, but which is aversive in a physically dependent subject.

There are no prior art reports disclosing controlled release formulations that do not employ opioid antagonists of one form or another and that might be capable of reducing the potential for abuse of narcotic analgesics.

The most successful extended release dosage forms comprise distinct structural elements that must be intact to function in controlled release manner. U.S. Pat. No. 3,845,770 describes an osmotic device for the zero-order release of an active agent. The osmotic device disclosed in this patent consists of an active agent enclosed in a semi-permeable wall. The semi-permeable wall is permeable to the passage of an external fluid but is substantially impermeable to the passage of the active agent in solution with the external fluid. An osmotic passageway is provided through the wall to deliver the solution of the active agent in the external fluid to the environment. U.S. Pat. No. 4,327,725 describes how to enhance the delivery kinetics of the basic osmotic pump via use of a hydrogel layer inside the semi-permeable membrane. U.S. Pat. No. 4,891,223 discloses a bioactive composition having a controlled, sustained release delivery pattern when contacted with a suitable surrounding media. The composition comprises a pharmaceutically, insecticidally, herbicidally or fertilizing bioactive material core, soluble in a given surrounding media, the core present in an amount at least sufficient for a total dosage during a treatment period; a first coating enveloping the bioactive material core comprising a polymer or a blend of polymers, said polymer or blend of polymers being swellable upon penetration by the surrounding media; and a second coating enveloping the first coating enveloped bioactive material core comprising a polymer or a blend of polymers; said polymer or blend of polymers being water-insoluble and forming a semi-permeable barrier permitting diffusion of the surrounding media into the first coating enveloped bioactive material core and also permitting the diffusion of the surrounding media dissolved bioactive material into the surrounding media.

The prior art discloses that microsphere matrices are useful for the preparation of pharmaceutical formulations, including extended release dosage forms. U.S. Pat. No. 4,837,381 discloses a microsphere composition of fat or wax or mixture thereof and a biologically active protein, peptide or polypeptide suitable for parenteral administration. U.S. Pat. No. 5,213,810 discloses water insoluble fat or wax microspheres containing biologically active protein, peptides or polypeptides wherein the fat or wax shell includes an oil, semi-soft fat or fatty acid derivative disclosed as stabilizing the microsphere by accelerating the formation of the beta crystal form of the fat or wax subsequent to spray atomization of the mixture. U.S. Pat. No. 3,080,293 discloses the preparation of niacinamide beadlets by admixing melted stearic acid with niacinamide powder passed through a centrifugal atomizer and spray chilled, dried and dusted with silicic acid.

US Patent Application No. 2001/0044026 discloses a microsphere composition comprising a water soluble core material in a matrix of water insoluble polymorphic shell material. Also disclosed is a process for the preparation of microspheres comprising subjecting a flowable mixture of core material and a first amount of water insoluble shell material to a pressure force to form a pressure-treated mixture, and passing said pressure-treated mixture through a spray nozzle into a chilling zone to form a solidified composition.

The prior art has not disclosed that microsphere matrices might be capable of reducing the potential for abuse of narcotic analgesics.

The abuse potential that this invention is intended to reduce is the abuse potential associated with the illicit, nonprescription or recreational use of a narcotic composition and the use of the compositions of this invention by other modes of administration such as the injection or inhalation of a crushed composition otherwise intended to be administered in intact form.

SUMMARY OF THE INVENTION

The present invention relates to an abuse-resistant controlled release pharmaceutical composition comprising a pharmaceutically effective amount of discrete particles of an active compound capable of abuse, wherein surfaces of said discrete particles are wetted with a coating material that is insoluble in water. A preferred composition further comprises a matrix in which said surface coated particles are distributed. The tamper-resistance of the composition matrix renders the composition difficult to alter and the abuse-potential compound, such as an opiate, contained within the matrix difficult to separate from the matrix. More preferred dosage forms are administered orally, preferably from once to four times a day.

Another aspect of present invention is a pharmaceutical composition comprising an opiate and a tamper-resistant matrix comprising one or more tenacious cross-linked polymers that are capable of bonding with the opiate such that the opiate is substantially incapable of immediate release from the polymer.

The use of the tamper-resistant composition renders the modified-release properties of the dosage form difficult to defeat as is commonly done in connection with drug abuse. The tamper-resistance of the dosage form does not depend on properties of the dosage form after it has been transformed into a different state, such as a gel by hydration, but rather on the physical and/or chemical properties of the composition or the matrix in its unaltered state as present in the dosage form.

Another aspect of the present invention relates to a method for the preparation of a controlled release pharmaceutical composition having a reduced potential for abuse, comprising applying a pressure force to a mixture comprising a water insoluble material, and particles of a pharmaceutically active compound capable of inducing in a subject a reaction that is physiologically or psychologically detrimental if administered in an immediate release dosage form, thereby resulting in surface coated particles; and incorporating said surface coated particles into a pharmaceutical composition.

DETAILED DESCRIPTION

The present compositions preferably deliver the abusable substance to the gastrointestinal tract gradually at the controlled rate intended for therapeutic effect. The potential for abuse that the present invention is designed to prevent is the inducing of a physiologically or psychologically detrimental effect, such as a "high", if the present composition were to be administered in an immediate release form. If an attempt were made to abuse the composition, in order to rapidly obtain the abuse inducing effect, for example by crushing the dosage form and ingesting the composition or administering it through some other portal, such as intravenously, the surface coated particles of abusable substance would inhibit any substantial increase in compound solubilzation and the occurrence of the abuse inducing effect. The surface coating material does not significantly affect or diminish the therapeutic effect of the abusable substance but is an integral part of the controlled release function of the present invention.

Most narcotics are significantly more potent when administered parenterally than orally, and intravenous abuse generally produces the desired abuse inducing effect more rapidly and with greater intensity than oral abuse and is, for many abusers, the preferred route of administration of an abusable substance. Thus, the use of the present invention can substantially reduce the potential for abuse of the compositions and dosage forms of this invention. More particularly, the compositions according to the present invention are resistant to abuse resulting from the application of mechanical stress such that the present stressed compositions are not capable, by oral, inhalation or intravenous means, of increasing substantially their immediate release of active compound having a potential for abuse.

The application of mechanical stress to the preferred abuse-resistant composition of the present invention results in an insubstantial increase in the immediate aqueous dissolution of active in said composition. More particularly, such application of stress increases the aqueous dissolution of active in the present compositions by less than about fifteen percent, and more preferably less than about ten percent, of the total pharmaceutically effective dosage amount in the first hour of in vitro dissolution testing. Furthermore, the dissolution rates of the preferred compositions are not substantially modified after the first hour of testing.

The mechanical stress applied to the compositions may be of any sort, and includes crushing, compressing, fracturing, tumbling, rolling, milling, and the like. A mechanical stress most likely to be used for abuse of said compositions is crushing.

Drugs having a potential for abuse include natural and synthetic narcotics and other psychoactive substances. A preferred embodiment of the present abuse-resistant composition comprises particles of compounds having a potential for abuse that are water-soluble, as the base compound or a pharmaceutically acceptable salt thereof. Preferred organic compound salts include pharmaceutically acceptable salts, such as mineral acid salts such as hydrogen halide acid salts such as hydrochloric acid salts, and phosphoric acid and sulfuric acid salts. Another class of preferred salts are the organic acid salts of organic bases, including the pharmaceutically acceptable carboxylic acids such as citric acid, tartaric acid, acetic acid, maleic acid, estoleic acid, succinic acid and the like.

The preferred abuse-resistant compositions of the present invention include one or more compounds that may be categorized as narcotic analgesics, or without limitation, analgesic agents such as pharmaceutically acceptable opiates and opiate-based derivatives that are suitable for use as a therapeutically effective analgesic, either alone or in combination with other substances. Examples of suitable opiates include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, and tramadol. The invention includes within its scope pharmaceutically acceptable salts of any of the foregoing and a mixture of two or more of any of the foregoing. Preferred agents include fentanyl, sufentanil, carfentanil, lofentanil, alfentanil, hydromorphone, oxycodone, hydroxycodone, propoxyphene, pentazocine, methadone, tilidine, butorphanol, buprenorphine, levorphanol, codeine, oxymorphone, meperidine, dihydrocodeinone and cocaine. Most preferred opiates include oxycodone, hydrocodone, codeine, morphine and petazocine, and pharmaceutically acceptable salts thereof. The particularly preferred opiate is oxycodone and pharmaceutically acceptable salts thereof.

The opiate component of the composition may include two or more opiates. For example, two or more opiates having different properties, such as half-life, solubility, potency, and a combination of any of the foregoing may be used. In preferred form, the analgesic of the composition comprises a single opiate or a combination of two or more opiates. However, the composition may include also or instead one or more non-opiate-based, therapeutically active ingredients as an analgesic. Such non-opiate-based therapeutically active ingredients may provide analgesia either alone or in combination with one or more opiates and include, for example: aspirin; acetaminophen; non-steroidal anti-inflammatory drugs ("NSAIDS"), for example, ibuprofen, and ketoprofen; N-methyl-D-aspartate receptor antagonists, for example, a morphinan such as dextromethorphan or dextrorphan, or ketamine; cyclooxygenase-II inhibitors ("COX-II inhibitors"); glycine receptor antagonists; and/or prostaglandin synthesis inhibitors.

In yet other embodiments of the present invention, one or more non-opiate-based active ingredients may be included to provide an effect other than analgesia, for example, an antitussive, expectorant, decongestant, antihistamine, hypnotic, sedative, CNS stimulant, or other class of compound, and mixtures of two or more of such compounds.

The opiate is included in the composition in a therapeutically effective amount. Such amount will vary in accordance with a number of factors including, for example, the particular species of opiate used, the presence of other ingredients, the specific form of the oral dosage formulation, and the particular application for which the composition is intended to be used. It is believed that in most applications, the amount of opiate included in the composition will be from about 0.1 to about 75 wt. %. In preferred form, the amount of opiate included in the composition will be from about 1 to about 50 wt. %, and even more preferably from about 1 to about 30 wt. %. When combined with other therapeutically active ingredients, the amount of opiate included in the composition will be from about 0.1 to about 20 wt. %, preferably from about 0.5 to about 15 wt. %, and even more preferably from about 1 to about 10 wt. %.

Microsphere compositions including such organic salts and prepared according to the present process are capable of linear release in an aqueous environment of about 50 to about 100 percent of the core material over a period of about 8 to about 24 hours. Preferred microspheres of the present invention are capable of linear release of about 70 to about 100 percent of the core material over a period of about 10 to about 14 hours, and most preferably about 12 hours. Another preferred composition is capable of linear release of about 80 to about 100 percent of the core material over a period of about 20 to about 26 hours, preferably about 22 to about 25 hours, and most preferably about 24 hours.

The particles of the compounds subject to potential abuse are surface coated in an "abuse reducing amount" if the amount of surface coating material is sufficient, when administered by at least one manner of potential abuse other than the manner by which the composition or dosage form is intended to be administered, to prevent or diminish the occurrence of the pharmacological effects of the abusable substance or to significantly delay the onset of these effects. If an attempt were made to abuse the composition by administration through some other portal, such as by inhalation or intravenous routes, the surface coating material would prevent the occurrence of the abuse inducing effect.

A preferred abuse-resistant composition according to the present invention comprises a matrix, throughout which the surface coated particles are distributed. In a special embodiment of the present invention, the material used to coat the surface of the particles comprises the matrix in which the particles are distributed.

The preferred pharmaceutical compositions include microspheres that comprise a matrix of pharmaceutically acceptable water insoluble material. The term "microsphere" as used herein is a particle in a variety of shapes including spherical, elongated or even rod-like spherical shape, and that has a diameter of the order of about 5-5000 microns, and most preferably from about 10 to 1000 microns, and most preferably from about 20 to about 800 microns. The preferred microspheres are substantially spherical in shape The more preferred pharmaceutical compositions comprise a water insoluble matrix material that is insoluble and resistant to degradation in the acidic pH conditions of the stomach. Such preferred compositions comprise microspheres, the surface of which is wrapped in such water insoluble material, does not exhibit the active on its surface, and is hence inherently enteric in structure. Most preferred compositions include microspheres wherein such surface characteristics are integral to the microsphere structure and do not comprise a separate coating layer to achieve such surface conditions.

A further preferred aspect of the present invention uses a water insoluble matrix material comprising a pH insensitive material, which include, but are not limited to, ethylcellulose, cellulose acetate, vinyl acetate/vinyl chloride copolymers, acrylate/methacrylate copolymers, polyethylene oxide, hydroxypropyl methylcellulose, hydroxyethyl cellulose, hydroxypropyl cellulose, triglycerides, hydrogenated vegetable oils, triglyceride polyalkoxyalkylesters, fats, waxes and water insoluble partially-degraded proteins.

A most preferred water insoluble matrix material comprises at least one component that is pH insensitive and that is digestible by enzymes present in the mammalian intestinal tract, most preferably the human intestinal tract. This aspect of the present invention is particularly useful for preferred pharmaceutical compositions of the present invention, which are preferably administered by the oral or rectal routes.

A particularly preferred aspect of the pharmaceutical composition includes a pH insensitive material that comprises one or more components digestible by enzymes present in the small intestine. In this regard, such materials are most preferred if they are digestible by the lipases present in the small intestine. Preferred materials include lipase degradable fats, waxes, triglycerides, hydrogenated vegetable oils, and triglyceride polyalkoxyalkylesters.

A special embodiment of the present invention comprises a matrix material that include at least two components, wherein one component is digestible in the small intestine, and a second component is indigestible in the small intestine. The digestible component may be a lipase-sensitive material, and is present in an amount from 100 percent by weight, to about 10 percent by weight based on the matrix material. A more preferred matrix composition comprises from about 5 to about 50 wt % of the digestible component, most preferably from 10 wt % to about 30 wt %, in combination with from about 95 wt % to about 50 wt %, and most preferably about 90 wt % to about 70 wt % of a small intestine indigestible or "lipase insensitive" component. Matrix compositions containing about 15 wt % to about 25 wt % of the digestible component are particularly preferred.

The small intestine indigestible or "lipase insensitive" component may be any material that is both pH insensitive and insensitive to the enzymes present in the gastrointestinal tract extending from the mouth until the cecum of the large intestine. Exemplary materials include, but are not limited to a water insoluble polysaccharide, a polyethylene glycol or glycol ether, or an indigestible wax or long chain aliphatic fatty acid ester. A particular embodiment of this component comprises a material that is digestible by enzymes present in the large intestine.

A preferred embodiment of the pharmaceutical composition comprises a matrix material that comprises from 2 to about 50 wt %, most preferably from 10 wt % to about 30 wt %, of an absorbable aliphatic alcohol having from about 8 to about 20 carbon atoms, in combination with small intestine indigestible or "lipase insensitive" component in an amount of from about 98 wt % to about 50 wt %, and most preferably about 90 wt % to about 70 wt %, based on the weight of the total material. A more preferred embodiment includes from about 5 to about 25 wt %, and most preferably about 15 wt % to about 20 wt % of the aliphatic alcohol. Most preferred alcohols are fatty acid alcohols, the most preferred being cetyl alcohol and stearyl alcohol.

Most preferred oral compositions release the active compound only after passing through the low pH environment of the stomach. Preferred embodiments of the present composition include release mechanisms programmed to deliver the active compound in the small intestine, the large intestine, or both. The location and timing of active release is by design. The compositions of the present invention are capable of releasing an enhanced amount of active compound in a continuous, sustained and controlled release rate.

A preferred matrix material is non-erodable at pH less than about 6. A further preferred aspect of the abuse-resistant composition comprises a matrix material that is erodable in the presence of bile salts and lipase.

The microsphere preferably comprises a water insoluble matrix of organic material that is resistant to dissolution or acidic degradation at pH levels found in the stomach, which pH is lower than about 4. The organic matrix material comprises a member selected from the group consisting of triglycerides, hydrogenated vegetable oils, polyalkoxyalkylethers, polyalkoxyalkylesters, water insoluble partially degraded proteins, digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils a wax or a mixture of waxes. Preferred hydrocarbons have a melting point of between 25 and 120.degree C., more preferred hydrocarbons having a melting point of 85 to 120 degrees C., and most preferred hydrocarbons have a melting point of between 95 and 120 degree C. Of these long chain hydrocarbon materials, fatty (aliphatic) alcohols are preferred. A preferred class of materials includes fats such as triglycerides and hydrogenated triglycerides derived from natural sources, and waxes. A particularly preferred class fats and waxes include the partially digestible and indigestible waxes, such as materials prepared from, for example, beeswax, paraffin, and carnauba waxes.

Particularly preferred water insoluble materials comprise a wax or a mixture of waxes. The water insoluble organic material preferably is a naturally derived or synthetically produced wax material, which may comprise a single chemical component or a mixture thereof. The term "wax" as used herein is intended to have as broad a meaning as possible and contemplates organic ester and waxy compounds derived from animal, vegetable, and mineral sources including modifications of such compounds from all three sources in addition to synthetically produced materials having similar properties. Examples of some of the waxes that may be used either alone or in combination with this invention include glyceryl tristearate, glyceryl distearate; Dynasan™ 110, 114, 116, 118; Sterotex™; canola wax/oil; cotton flakes; soya flakes; castor wax; rapeseed wax; beeswax; carnauba wax; candelilla wax; microwax (petroleum Boler™ Wax 1014 based); Dritex C™; special Fat™ 42, 44, 168 t; Be Square™ Wax #195a; Be Square™ Wax #195w; Energybooster™; Astor™ Wax 180; Astor™ Wax 150; and polyethylene.

Fats are the commonly used class of waxes and preferred in particular embodiments of the present invention are known as the triglycerides. In nature, triglycerides are usually found in complex mixtures. Depending upon the source of the triglyceride, whether animal or plant, the triglyceride may be formed from shorter or longer carboxylic acids which may in turn be either saturated or unsaturated. Triglycerides formed from shorter chain, unsaturated carboxylic acids, as a rule, melt at a lower temperature than triglycerides formed from longer-chain, saturated acids. In most cases, triglycerides are formed of more than one type of carboxylic acid. Further, the physical characteristics of a triglyceride (such as whether it exists as a liquid or solid at room temperature) are determined not only by which carboxylic acids were incorporated by esterification but also in which of the glyceryl hydroxy positions a given carboxylic acid was incorporated. Thus, animal triglycerides differ from plant triglycerides not so much in the overall ratios of saturated to unsaturated acids or of acids of given lengths, but rather in which of the three hydroxy positions in the glyceryl molecule unsaturated acids are to be found. Also, typically, naturally occurring triglyceride waxes, which are solid at room temperature, do not display a single sharp melting point because of the wide range of triglycerides present in most natural products.

Triglyceride waxes may be obtained commercially with a choice of chain length of the carboxylic acids that form the triglycerides, as well as a choice of purity grades. Commercial preparations of triglycerides start with natural products in which a number of different triglycerides are associated with each other. Processing not only saturates the acid substituents but also reduces the variety of triglycerides in the final material. The method and apparatus of this invention may be clearly demonstrated using the monoacid triglyceride, glyceryl tristearate ("tristearin") formed by the esterification of 18-carbon stearic acids with all three hydroxy groups of glyceryl. Stearic acid is a fully saturated carboxylic acid. One suitable commercial grade of tristearin is a product having the trademark "Dynasan™ 118" which is manufactured by Dynamit Nobel, a subsidiary of Hulls America. Dynasan™ 118 is a highly purified material from a vegetable source that contains relatively few triglyceride molecules that have esterified acids of different lengths. Similar, although somewhat less pure triglyceride materials, are also commercially available under the trademark Sterotex™. As the manufacturer supplies it, Dynasan 118 is a white microcrystalline powder crystallized in the beta form, the DSC of which exhibits a single endothermic peak centered at approximately 72.degree. C. indicating that only a single polymorphic form is present with a melting point within the melting point temperature range of the beta. form. Other preferred triglyceride waxes include Dritex C, a hydrogenated cottonseed oil wax, and BF117 (Bakers Flake 117) now sold as Shurset 117, partially hydrogenated soybean oil, both of which are sold commercially by AC Humko.

The preferred water insoluble matrix material melts between about 120 degrees F. and about 225 degrees F., and preferably between about 189 degrees and 220 degrees F., and most preferably between about 200 and about 220 degrees F. A single endothermic peak in the melting curve of the matrix material is preferred, although not required. A relatively sharp melting point peak is most preferred.

The surface coating, or matrix material may also comprise a polyalkylene glycol. One suitable controlled release coating material comprises at least one water insoluble material such as an alkyl-cellulose (especially ethyl cellulose), and, optionally, at least one polyalkylene glycol, the amount of which present in the dosage form will be determined, as above, by the rate of opioid release required. It will also depend on whether at least one polyalkylene glycol is present in or absent from the oral dosage form. Another suitable controlled-release matrix would comprise an alkyl-cellulose $C_{12}$ to $C_{36}$ aliphatic alcohol and, optionally, a polyalkylene glycol.

In certain preferred embodiments of the present invention, the surface coating material comprises a hydrophobic polymer such as a pharmaceutically acceptable acrylic polymer, including but not limited to acrylic acid and methacrylic acid copolymers, methyl methacrylate copolymers, ethoxyethyl methacrylates, cyanoethyl methacrylate, aminoalkyl methacrylate copolymer, poly(acrylic acid), polymethacrylic acid, methacrylic acid alkylamide copolymer, poly(methyl methacrylate), poly(methacrylic acid anhydride), methyl methacrylate, polymethacrylate, polyacrylamide and glycidyl methacrylate copolymers. In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic coating is derived from an acrylic resin lacquer, such as that which is commercially available form Rohm Pharma under the Tradename Eudragit.™. In further preferred embodiments, the acrylic coating comprises a mixture of two acrylic resin lacquers commercially available from Rohm Pharma under the Tradenames Eudragit.™. RL 30 D and Eudragit™. RS 30 D, respectively. Eudragit™. RL 30 D and Eudragit™. RS 30 D are copolymers of acrylic and methacrylic esters with a low content of quaternary ammonium groups, the molar ratio of ammonium groups to the remaining neutral (meth)acrylic esters being 1:20 in Eudragit™. RL 30 and 1:40 in Eudragit™. RS 30 D. The mean molecular weight is about 150,000. The code designations RL (high permeability) and RS (low permeability) refer to the permeability properties of these agents. Eudragit.™. RL/RS mixtures are insoluble in water and in digestive fluids. However, coatings formed from the same are swellable and permeable in aqueous solutions and digestive fluids.

The Eudragit™ RL/RS dispersions of the present invention may be mixed together in any desired ratio in order to ultimately obtain a surface coating formulation having a desirable dissolution profile. Desirable sustained-release formulations may be obtained, for instance, from a retardant coating derived from 100% Eudragit™. RL, 50% Eudragit™. RL and 50% Eudragit™. RS, and 10% Eudragit™. RL:Eudragit™. 90% RS. Of course, one skilled in the art will recognize that other acrylic polymers may also be used, such as, for example, Eudragit™. L.

In other preferred embodiments, the hydrophobic polymer that may be used for coating the surfaces of the particles capable of abuse is a hydrophobic cellulosic material such as ethylcellulose. Those skilled in the art will appreciate that other cellulosic polymers, including other alkyl cellulosic polymers, may be substituted for part of all of the ethylcellulose included in the hydrophobic polymer coatings of the present invention.

One commercially-available aqueous dispersion of ethylcellulose is Aquacoat™. (FMC Corp., Philadelphia, Pa., U.S.A.). Another aqueous dispersion of ethylcellulose is commercially available as Surelease™. (Colorcon, Inc., West Point, Pa., U.S.A.). A hot melt of a polymer, plasticizer (dibutyl sebacate), and stabilizer (oleic acid) is prepared as a homogeneous mixture, which is then diluted with an alkaline solution to obtain an aqueous dispersion which can be applied directly sprayed onto the particle surfaces.

In embodiments of the present invention where the coating is derived from an aqueous dispersion of a hydrophobic polymer, the inclusion of an effective amount of a plasticizer in the aqueous dispersion of hydrophobic polymer will further improve the physical properties of the film. For example, because ethyl-cellulose has a relatively high glass transition temperature and does not form flexible films under normal coating conditions, it is necessary to plasticize the ethylcellulose before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, acetyl triethyl citrate, tributyl citrate, and triacetin, although it is possible that other water-insoluble plasticizers (such as acetylated monoglycerides, phthalate esters, castor oil, etc.) may be used. Triethyl citrate is especially preferred.

Examples of suitable plasticizers for the acrylic polymers of the present invention include citric acid esters such as triethyl citrate NF XVI, tributyl citrate, dibutyl phthalate, and possible 1,2-propylene glycol, polyethylene glycols, propylene glycol, diethyl phthalate, castor oil, and triacetin, although it is possible that other water-insoluble plasticizers (such as acetylated monoglycerides, phthalate esters, castor oil, etc.) may be used. Triethyl citrate is especially preferred.

When the coating comprises an aqueous dispersion of ethylcellulose, the particles are preferably coated and subsequently cured at a temperature greater than the glass transition temperature of the coating solution (i.e., ethylcellulose) and at a relative humidity from about 60% to about 100%, until the curing endpoint is reached, e.g., about 60.degree. C. and a relative humidity from about 60% to about 100% for a time period from about 48 to about 72 hours.

In one preferred embodiments of the present invention directed to the acrylic coating, a surface coated product is obtained by coating the surfaces of the particles of at a temperature above the Tg of the plasticized acrylic polymer for the required time period, the optimum values for temperature and time for the particular formulation being determined experimentally. In certain embodiments of the present invention, the surface coated product is obtained at a temperature of about 100.degree C. The matrix composition comprises from 0 to about 50-wt % of a water insoluble polysaccharide, a polyethylene glycol or glycol ether, or a second indigestible wax, based on the weight of the total material.

A most preferred matrix composition comprises from about one to about 50 wt % of an aliphatic alcohol having from about 8 to about 20 carbon atoms, based on the weight of the total material. A particularly preferred alcohol is a fatty acid alcohol. Most preferred alcohols include stearyl alcohol and cetyl alcohol.

In another embodiment, the opiate component is chemically bonded to the matrix. In a further embodiment, the tamper-resistant properties of the composition are the result of a combination of both the physical arrangement and the chemical bonds between the opiate component and the matrix. In such an embodiment, the combination may be achieved by means of a single material comprising the matrix or by means of a combination of two or more materials. In all of these embodiments, sustained-release properties of the composition are preferably realized by providing either pore- or erosion-controlled release of the opiate from the matrix or by degradation by gastrointestinal fluids. Those embodiments in which highly cross-linked polymers are used as the matrix, the tenacity of the composition is due to the hardness of the matrix. In alternative embodiments in which low cross-linked polymers or viscoelastic polymers are used as the matrix, the tenacity of the composition is due to the elasticity of the matrix. In these embodiments, matrix tenacity, or resistance to opiate component release, is imparted to the composition by the use of pharmaceutically acceptable cross-linked polymers such as cholestyramine resin.

The oral dosage form may further include one or more active ingredients in addition to the opiate, which additional active ingredients may or may not act synergistically therewith. In one embodiment, a combination of two or more opiates may be included in the oral dosage form. For example, the dosage form may include two opiates having different properties, such as half-life, solubility, potency, and a combination of any of the foregoing. In another embodiment, one or more opiates are combined in the dosage form with one or more non-opiate drugs. Such non-opiate drugs would preferably provide additional analgesia, and include, for example, aspirin; acetaminophen; NSAIDS, such as ibuprofen, ketoprofen, etc.; N-methyl-D-aspartate receptor antagonists, such as a morphinan such as dextromethorphan or dextrorphan, or ketamine; COX-II inhibitors; glycine receptor antagonists; and/or prostaglandin synthesis inhibitors. In such embodiments, the present invention may provide for the analgesically effective use of lower doses of the opiate by virtue of the inclusion of one or more additional non-opiates, such as, for example, an NSAID or a COX-2 inhibitor. By using lower amounts of either or both drugs, the side effects associated with higher dosages may be reduced.

Suitable NSAIDS include ibuprofen, acemetacin, aminoprofen, benoxaprofen, bucloxic acid, carprofen, clidanac, diclofenac, diflunisal, diflurisal, etodolac, fenoprofen, fentiazac, flubufen, flufenamic acid, flufenisal, fluprofen, flurbiprofen, indomethacin, indoprofen, isoxicam, ketoprofen, ketorolac, meclofenamate, meclofenamic acid, mefenamic acid, meloxicam, muroprofen, nabumetone, naproxen, niflumic acid, oxaprozin, oxpinac, piroprofen, piroxicam, pramoprofen, salsalate, sudoxicam, sulindac, suprofen, tiaprofenic acid, tiopinac, tolfenamic acid, tolmetin, trioxaprofen, zidometacin or zomepirac, and the like. Useful dosages of these drugs are well known to those skilled in the art.

In yet further embodiments, a non-opiate drug can be included in the oral dosage form, which provides a desired effect other than analgesia. Examples of such therapeutically active agents include antihistamines (e.g., dimenhydrinate, diphenhydramine, chlorpheniramine and dexchlorpheniramine maleate), anti-emetics (e.g., metoclopramide, methylnaltrexone), anti-epileptics (e.g., phenyloin, meprobamate and nitrazepam), vasodilators (e.g., nifedipine, papaverine, diltiazem and nicardipine), anti-tussive agents and expectorants (e.g., codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluthiazide), anti-hypotensives (e.g., propranolol, clonidine), antihypertensives (e.g, clonidine, methyldopa), bronchodilators (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, vitamins, stimulants (including appetite suppressants such as phenylpropanolamine), as well as salts, hydrates, and solvates of the same.

The present invention also relates to the process for the manufacture of the present microspheres. The present sustained release pharmaceutical compositions having a reduced potential for abuse may be prepared by applying a pressure force to a mixture comprising particles of a compound having a potential for abuse and a water insoluble material thereby resulting in surface coated particles and incorporating the resulting surface coated particles into a pharmaceutical composition that when subjected to stress does not increase substantially the immediate release of said compound in an aqueous environment.

A particularly preferred method is wherein the aforesaid pressure force is applied to a dispersion of said particles in a flowable water insoluble medium.

The pressure force applied to the aforesaid dispersion may be in the form of an abrupt high pressure force caused by the compression of a piston, or an ultrasonic device. The preferred pressure force is applied to the dispersion in accordance with the method and apparatus (Beta apparatus) described in U.S. Pat. No. 5,209,879, which is hereby incorporated by reference. The compressive forces are generated by compacting the dispersion during a short time interval and forcing the compacted dispersion through the "beta" chamber thereby subjecting the mixture to a shear and cavitation forces resulting from the high-pressure surges and currents created in a post pressure reduction chamber. This process is described in U.S. Pat. Nos. 4,978,483, 5,460,756, and 5,209,879 all hereby incorporated by reference. The amount of pressure force required, in the present invention, depends on the time interval during which the pressure is applied. The required pressure varies inversely with that time interval. The pressure pulse process continues as long as the pressure is maintained on the dispersion, but the matrix dispersion is most effective when the pressure is applied for a very short period of time, preferably on the order of one second or less. To amplify the effectiveness of the pressure force processing, the pressure-treated mixture may be repeatedly subjected to the application of pressure in the Beta apparatus. The flowable composition may be passed through the Beta apparatus one, two or even three times to achieve the desired effect size reduction and encapsulation.

A special embodiment of the present invention forms microspheres from the surface-coated particles by the process of spraying, into a chilling zone maintained as a temperature below the solidification temperature of the water insoluble fluid matrix material, a flowable dispersion of active particles in the water insoluble fluid matrix. A most preferred process employs conditions that impart an electrostatic charge to said water insoluble matrix and that form droplets of said dispersion. The process preferably maintains the fluidity of, and charge on, the droplets for a time sufficient to distribute the particles electrostatically within the droplets, prior to the solidification of the droplets into microspheres.

The temperature of the fluid mixture as it reaches the spray nozzle should be maintained below the melting temperature of said matrix material but above its solidification temperature. The temperature of the spraying, the configuration of the spray nozzle, and the flow rate through the nozzle all influence the physical characteristics of the resulting microspheres. A most preferred process uses a heated spray nozzle (and heated tubings and conduits leading up to said nozzle) that ensures that the pressure-treated mixture maintains a viscosity suitable for a high spray throughput. Such high throughput enables the formation of substantially spherical microspheres upon cooling the sprayed particles of liquid mixture below the solidification temperature of the matrix material.

The flowable matrix material most preferably exhibits a melting curve where melting begins at T1 and is substantially complete at T2, and exhibits a cooling curve where solidification begins at T3 and is substantially complete at T4, wherein T3 is less than T1. The difference between T1 and T2 for any particular matrix material used in the present method is determined by the ratio of materials comprising said flowable medium matrix. By modifying the ratio of components, the temperature characteristics, and hence release characteristics, of the microspheres produced by the present method, may be predetermined. Furthermore, by determining the melting and solidification temperatures for the particular matrix material used in the present method, the temperatures of the mixture during treatment may be adjusted accordingly to avoid jamming or clogging of the apparatus during operation.

The preferred process utilizes a water insoluble organic matrix material that melts between about 90 degrees F. and about 225 degrees F., and the process maintains the flowable dispersion at a temperature above the solidification temperature of said water insoluble medium, but below the melting temperature of said water insoluble medium. A more preferred process employs a water insoluble matrix having a melting point that starts at about 95 degrees F. and is substantially complete at about 140 degrees F.

Further processing of the formed microspheres may include contact with a second amount of water insoluble material soluble at pH greater than about 6. A preferred means of accomplishing this contacting is with spray coating. The pH>6 material applied may comprise from about 5 to about 30 percent by weight of said water insoluble matrix material used to form said solidified microsphere, and preferably the pH>6 material is about 10 percent by weight of said second amount of said water insoluble matrix material.

A particularly preferred process further comprises annealing said solidified composition. Annealing may comprise heating the solidified composition to a temperature less than the melting point of the water insoluble organic material for a period of time ranging from about one minute to about four hours. The annealing time is variable depending on the particular organic material used. Annealing is particularly preferred when said water insoluble material is capable of solidifying into more than one crystalline form, such as a polymorphic material, for example, when said polymorphic material comprises a triglyceride wax.

The sustained release rate is believed to occur due to the erosion of minute imperfections in the microspheres of the present invention which form "tortuous" paths throughout the matrix of the inner encapsulate thereby providing ingress of aqueous media and egress of solubilized capsules.

Microspheres formed from the process according to the present invention are range in size from about 50 to about 900 microns in size, and may have a variety of shapes including spherical, elongated, or even rod-like. The preferred microspheres are substantially spherical in shape, and have an average particle size of between about 150 to about 800 microns. Depending on the application, preferred microspheres have an average particle size of 50 to 250 microns include particles of active compound having an average particle size of about 10 to about 50 microns. In other applications, the more preferred microspheres have an average particle size of about 300 microns to about 500 microns, and most preferably from about 300 to about 450 microns.

The release properties of the microspheres prepared using the aforesaid two-step process is a function of the percentage of active particles in the microsphere matrix composition, the size and shape of the microsphere, and the matrix composition.

The release of the active compound from the sustained-release formulation of the present invention can be further influenced, by admixing the surface coated particles with the addition of one or more release-modifying agents. The ratio of hydrophobic polymer to water soluble material is determined by, among other factors, the release rate required and the solubility characteristics of the materials selected.

The release-modifying agents that function as pore-formers may be organic or inorganic, and include materials that can be dissolved, extracted or leached from the coating in the environment of use. The pore-formers may comprise one or more hydrophilic polymers such as hydroxypropylmethylcellulose.

The sustained-release compositions of the present invention can also include erosion-promoting agents such as starch and gums.

The release-modifying agent may also comprise a semi-permeable polymer.

In certain preferred embodiments, the release-modifying agent is selected from hydroxypropylmethylcellulose, lactose, metal stearates, and mixtures of any of the foregoing.

The methods according to the present invention relate to administering a sustained-release pharmaceutical composition containing active compound to a patient in need thereof, comprising administering to said subject a pharmaceutically effective amount of composition including the microspheres comprising the surface coated active compound described hereinabove. For purposes of the present invention, the sustained release compositions of the present invention release the opiate from the matrix at such a rate that blood plasma concentrations of the opiate are maintained within the therapeutic range (above the minimum effective analgesic concentration), but below toxic levels, over a period of time of about 8 to about 36 hours, and preferably about 5 to about 24 hours. A most preferred method provides for the administration of a composition wherein the active compound is released to said patient over a period of time preferably from about 8 to about 24 hours, and alternatively about 12 to about 30 hours, and most preferably from about 18 to about 24 hours.

The compositions of the present invention comprise optionally a vehicle, the nature of which will depend on the form of the composition. The microspheres of the present composition can be used in any suitable form, for example, compressed in the form of a tablet, in the form of multiparticulates filled in a capsule and suspended in a liquid carrier. Aside from the sustain release properties of the composition of the present invention, the tablets and capsules can be further modified to provide additional delayed release, sustained release, or immediate release characteristics. It is believed that the composition of the present invention will be used most widely in solid oral dosage form.

The term "vehicle" is used broadly to include various types of pharmaceutically acceptable ingredients that can comprise the composition other than the active compound and polymer and/or the aliphatic alcohol constituents of the composition. Examples of vehicles include fillers, diluents, excipients and materials, which have an effect on the release properties of the active compound, that is, control-release materials.

Fillers or bulking agents include, but are not limited to, microcrystalline cellulose (e.g., Avicel™., FMC Corp., Emcocel™, Mendell Inc.), mannitol, xylitol, dicalcium phosphate (e.g. Emcompress, Mendell Inc.) calcium sulfate (e.g. Compactrol, Mendell Inc.) starches, lactose, sucrose (Dipac, Amstar, and Nutab, Ingredient Technology), dextrose (Emdex, Mendell, Inc.), sorbitol, cellulose powder (Elcema, Degussa, and Solka Floc, Mendell, Inc.) The bulking agent may be present in the composition in an amount of from about 5 wt. % to about 90 wt. %, preferably from about 10 wt. % to about 50 wt. %.

Disintegrating agents that may be included in the composition include, but are not limited to, microcrystalline cellulose, starches, crospovidone (e.g. Polyplasdone XL, International Specialty Products.), sodium starch glycolate (Explotab, Mendell Inc.), and crosscarmellose sodium (e.g., Ac-Di-Sol, FMC Corp.). The disintegrating agent may be present in the composition in an amount of from about 0.5 wt. % to about 30 wt %, preferably from about 1 wt. % to about 15 wt. %.

Antiadherants and glidants which may be employed in the composition include, but are not limited to, talc, corn starch, silicon dioxide, sodium lauryl sulfate, and metallic stearates. The antiadherant or glidant may be present in the composition in an amount of from about 0.2 wt. % to about 15 wt. %, preferably from about 0.5 wt. % to about 5 wt. %.

Lubricants which may be employed in the composition include, but are not limited to, magnesium stearate, calcium stearate, sodium stearate, stearic acid, sodium stearyl fumarate, hydrogenated cotton seed oil (Sterotex), talc, and waxes, including but not limited to, beeswax, carnauba wax, cetyl alcohol, glyceryl stearate, glyceryl palmitate, glyceryl behenate, hydrogenated vegetable oils, and stearyl alcohol. The lubricant may be present in an amount of from about 0.2 wt. % to about 20 wt. %, preferably from about 0.5 wt. % to about 5 wt. %.

Binding agents which may be employed include, but are not limited to, polyvinyl pyrrollidone, starch, methylcellulose, hydroxypropyl methylcellulose, carboxymethyl cellulose, sucrose solution, dextrose solution, acacia, tragacanth and locust bean gum. The binding agent may be present in the composition in an amount of from about 0.2 wt. % to about 10 wt. %, preferably from about 0.5 wt. % to about 5 wt. %.

The compositions of the present invention may be made by a direct compression method, or by a wet granulation method. In the direct compression method, the microspheres and other ingredients are sieved through a stainless steel screen, such as a 40 mesh steel screen. The sieved materials then are charged to a suitable blender, and blended for 10 minutes with an intensifier bar on for 3 minutes. The blend then is compressed into tablets on a rotary press using appropriate tooling. The compressed tablets may be coated, if desired.

In the wet granulation method, the microspheres and other ingredients are granulated with a granulating fluid (e.g., isopropyl alcohol, ethyl alcohol, and water) in a planetary mixer, high shear mixer, or fluidized bed granulator. Binding agents may be contained in the granulating fluid, or may be in the dry mix. The wet granules are dried in an oven or fluidized bed dryer, and then sieved through a suitable screen to obtain free flowing granules. The resulting granules were blended with a suitable lubricant and glidant, and the lubricated granules are compressed into tablets on a rotary press using appropriate tooling. If desired, a coating can be applied onto the compressed tablets.

In certain embodiments of the present invention, an effective amount of opioid in immediate release form is included in the unit dose comprising the substrates of the present invention. In embodiments in which the opiate comprises oxycodone, the oral dosage form may include analgesic doses from about 10 mg to about 360 mg, preferably from about 10 mg to about 160 mg, of oxycodone per unit dose. In general, the immediate release form of the opioid is included in an amount, which is effective to shorten the time to maximum concentration of the opioid in the blood (e.g., plasma), such that the Tmax is shortened to a time of, e.g., from about 2 to about 4 hours. This causes the blood concentration curve to have an early peak rather than the substantially flattened curves currently recommended by those skilled in the art. It has been discovered that by including such an effective amount of immediate release opioid in the unit dose, the experience of relatively higher levels of pain in patients is significantly reduced. In such embodiments, an effective amount of the opioid in immediate release form may be included in the compositions of the present invention. For example, where the extended release opioid from the formulation is due to surface-coated particles, the immediate release component would be admixed therewith. Where a plurality of the microspheres comprising an effective unit dose of the opioid are incorporated into a hard gelatin capsule, the immediate release portion of the opioid dose may be incorporated into the gelatin capsule via inclusion of the sufficient amount of immediate release opioid as a powder or granulate within the capsule. Alternatively, the gelatin capsule itself may be coated with an immediate release layer of the opioid. One skilled in the art would recognize still other alternative manners of incorporating the immediate release opioid portion into the unit dose. Such alternatives are deemed to be encompassed by the appended claims.

The multiparticulate unit dose of therapeutically effective compound may be contained within a hard gelatin capsule. Alternatively, the multiparticulate unit dose may be prepared as other dosage forms known to those skilled in the art, including sachets. The hard gelatin capsule may be opened and the powder-layered beads containing the drug may be sprinkled into fluids or mixed with food, in particular cool, soft food, such as applesauce or pudding, or a liquid such as water or orange juice.

EXAMPLES

Example 1

428 g of milled hydroxycodone HCl (<10 micron particle size) is mixed into a melt of 800 g of Dritex C, a commercially available polymorphic wax. The flowable dispersion is subjected to a pressure-force by passing it twice through a hydraulic piston driven pump, the "Beta" machine described in U.S. Pat. No. 5,209,879, set at 90 psi (Beta chamber configuration=entrance nozzle consisting of 4 holes (0.02 in ID), a chamber volume formed of spacers with a length of about 0.04 in and a diameter of about 0.25 in, and an exit nozzle consisting of four holes (0.02 in ID)). The pressure-treated mixture is sprayed through a Nordson hot melt applicator maintained at 77 degrees C., driven by an electronic gear pump (Nordson 3700 series, speed setting=40%), aspirator pressure of 10 psi, needle set at 7/8 of a turn open from closed, into a chilled area. The hydroxycodone HCl comprises 34.9% by weight of the microsphere composition.

Example 2

472.5 g of milled hydroxycodone HCl (<10 micron particle size) is mixed into a melt of a mixture of 975 g of carnuba wax and 52.5 g of xanthan gum. The flowable dispersion is then subjected to a pressure-force by passing it twice through a hydraulic piston driven pump, the "Beta" machine described in U.S. Pat. No. 5,209,879, set at 90 psi (Beta chamber configuration=entrance nozzle consisting of 4 holes (0.02 in ID), a chamber volume formed of spacers with a length of about 0.04 in and a diameter of about 0.25 in, and an exit nozzle consisting of four holes (0.02 in ID)). The pressure-treated mixture is sprayed through a Nordson hot melt applicator maintained at 123 degrees C., driven by an electronic gear pump (Nordson 3700 series, speed setting=50%), aspirator pressure of 10 psi, needle set at 1.5 turn open from closed, into a chilled area. The hydroxycodone HCl comprises 31.5% by weight of the microsphere composition.

Example 3

268 g of unmilled hydroxycodone HCl is mixed into a melt of 520 g of Dritex C, a commercially available polymorphic wax. The flowable dispersion is subjected to a pressure-force by passing it twice through a hydraulic piston driven pump, the "Beta" machine described in U.S. Pat. No. 5,209,879, set at 90 psi (Beta chamber configuration=entrance nozzle consisting of 4 holes (0.02 in ID), a chamber volume formed of spacers with a length of about 0.04 in and a diameter of about 0.25 in, and an exit nozzle consisting of four holes (0.02 in ID)). The pressure-treated mixture is sprayed through a Nordson hot melt applicator maintained at 77 degrees C. at a pump speed of 30%, aspirator pressure of 10 psi, needle set at 1.5 turn open from closed, into a chilled area. The hydroxycodone HCl comprises about 34% by weight of the microsphere composition.

Example 4

54 g of milled hydrocodone bitartrate (<10 micron particle size) is mixed into a melt of a mixture of 975 g of carnuba wax and 52.5 g of xanthan gum. The flowable pre-mixture is then subjected to a pressure-force by passing it twice through a hydraulic piston driven pump, the "Beta" machine described in U.S. Pat. No. 5,209,879, set at 90 psi (Beta chamber configuration=entrance nozzle consisting of 4 holes (0.02 in ID), a chamber volume formed of spacers with a length of about 0.04 in and a diameter of about 0.25 in, and an exit nozzle consisting of four holes (0.02 in ID)). The pressure-treated mixture is sprayed through an air-atomizing nozzle maintained at 123 degrees C., from a closed vessel with top displacement air pressure of 2 psi, aspirator pressure of 10 psi, into a temperature-maintained chamber. The composition comprises microspheres containing 5% by weight of hydrocodone bitartrate.

Example 5

58 g of unmilled hydrocodone bitartrate is mixed into a melt of 520 g of Sterotex, NF, a commercially available polymorphic wax. The flowable pre-mixture is then subjected to a pressure-force by passing it twice through a hydraulic piston driven pump, the "Beta" machine described in U.S. Pat. No. 5,209,879, set at 90 psi (Beta chamber configuration=entrance nozzle consisting of 4 holes (0.02 in ID), a chamber volume formed of spacers with a length of about 0.04 in and a diameter of about 0.25 in, and an exit nozzle consisting of four holes (0.02 in ID)). The pressure-treated mixture is sprayed through an air-atomizing nozzle maintained at 77 degrees C., from a closed vessel with top displacement air pressure of 2 psi, aspirator pressure of 10 psi, into a temperature-maintained chamber. The composition comprises microspheres containing about 10% by weight of hydrocodone bitartrate.

Example 6

108 g of milled hydrocodone bitartrate (<10 micron particle size) is mixed into a melt of a mixture of 975 g of carnuba wax and 52.5 g of pectin. The flowable pre-mixture is then subjected to a pressure-force by passing it twice through a hydraulic piston driven pump, the "Beta" machine described in U.S. Pat. No. 5,209,879, set at 90 psi (Beta chamber configuration=entrance nozzle consisting of 4 holes (0.02 in ID), a chamber volume formed of spacers with a length of about 0.04 in and a diameter of about 0.25 in, and an exit nozzle consisting of four holes (0.02 in ID)). The pressure-treated mixture is sprayed through an air-atomizing nozzle maintained at 123 degrees C., from a closed vessel with top displacement air pressure of 2 psi, aspirator pressure of 10 psi, into a temperature-maintained chamber. The composition comprises microspheres containing about 10% by weight of hydrocodone bitartrate.

Example 7

Crushing Dissolution Comparison

Microsphere compositions including water-soluble drug and prepared using the methods described in the above Examples are ground (stressed) using a mortar and pestle. Stressed and unstressed samples are examined microscopically and tested for drug release rates. Comparisons are made between the two prepared samples.

The microspheres are subjected to three different degrees of crushing.

The ground samples exhibit deformed and fractured microspheres with a distribution from fine to large fragments. Some intact microspheres continue to be present in the mildly crushed sample. The unground samples are spherical and uniform (as per the −20+40 mesh fraction taken) as originally manufactured.

Dissolution of the water-soluble active ingredient from ground and unground samples is determined. The ground sample is characterized by a two-phase release rate, including an initial burst phase of short duration, followed by a second release phase, which is constant over the remaining test period. The unground sample is characterized by a single phase, constant release rate over the entire test period without a burst period. The drug release rates for the ground samples following the burst period, and the unground sample are very similar. Greater crushing shows only a small increase in the burst with additional stress, while the rate of release remained the same thereafter.

The matrix material appears to be very closely associated with the drug particle surface, wetting the drug particle surface, and is not simply admixed with the particles. Each drug particle can be viewed as being individually encapsulated by matrix material, independent of the presence of any third encapsulating component. The matrix can serve the encapsulating function itself. Also, the grinding appears to only disturb the initial dissolution delay function of the microspheres. It also suggests that the matrix material retains its elastic-like nature through the manufacturing process.

We claim:

1. An abuse-resistant controlled-release pharmaceutical composition comprising a plurality of microspheres, each microsphere comprises:
   (i) a water insoluble matrix material, and
   (ii) a plurality of discrete particles distributed throughout the water insoluble matrix material, each particle comprises a pharmaceutically effective amount of an active water soluble compound capable of abuse and having surfaces that are wetted with a coating of the water insoluble matrix material,
   wherein said water insoluble matrix material is present in an abuse-reducing amount whereby crushing, compressing, fracturing, tumbling, rolling, or milling of said controlled-release pharmaceutical composition results in an increase in the aqueous dissolution of said active water soluble compound by less than about 15% of the total pharmaceutically effective amount of the active water soluble compound in the composition in the first hour of in vitro dissolution testing,
   wherein the water soluble compound capable of abuse is an opioid agonist, and
   wherein the composition does not include an antagonist of the water soluble compound capable of abuse.

2. The abuse-resistant composition according to claim 1 wherein said matrix material is non-erodable at pH less than about 6.

3. The abuse-resistant composition according to claim 2 wherein said matrix material is erodable in the presence of bile salts and lipase.

4. The abuse-resistant composition according to claim 1 wherein crushing said matrix before contacting with water increases the aqueous dissolution of active water soluble compound in said composition by less than about 10% of the total pharmaceutically effective amount of the active water soluble compound in the composition in the first hour of in vitro dissolution testing.

5. The abuse-resistant controlled-release pharmaceutical composition according to claim 1 for administration to a subject in need thereof from once to four times a day.

6. The dosage form according to claim 1 wherein said opioid agonist is selected from the group consisting of fentanyl, sufentanil, carfentanil, lofentanil, alfentanil, hydromorphone, oxycodone, hydroxycodone, propoxyphene, methadone, tilidine, butorphanol, buprenorphine, levorphanol, codeine, oxymorphone, meperidine, dihydrocodeinone and cocaine.

7. The abuse-resistant composition of claim 1, wherein the matrix material is a triglyceride wax selected from the group consisting of a hydrogenated cottonseed oil wax, a partially hydrogenated soybean oil, carnuba wax or a mixture thereof.

* * * * *

UNITED STATES PATENT AND TRADEMARK OFFICE
CERTIFICATE OF CORRECTION

PATENT NO. : 8,623,412 B2
APPLICATION NO. : 10/528727
DATED : January 7, 2014
INVENTOR(S) : Vaghefi et al.

It is certified that error appears in the above-identified patent and that said Letters Patent is hereby corrected as shown below:

On the Title page, item 12, replace "Farid et al." with --Vaghefi et al.--.

On the Title page, item 75, Inventor, replace "Vaghefi Farid" with --Farid Vaghefi--.

Signed and Sealed this
Twenty-third Day of June, 2015

Michelle K. Lee
*Director of the United States Patent and Trademark Office*